United States Patent [19]

Fukukawa et al.

[11] Patent Number: 4,816,575
[45] Date of Patent: * Mar. 28, 1989

[54] 2'-(R)-SUBSTITUTED-2'-DEOXYNEPLANO-CIN A DERIVATIVES

[75] Inventors: Kiyofumi Fukukawa, Hokkaido; Takao Hirano; Masatoshi Tsujino, both of Shizuoka; Tooru Ueda, Hokkaido, all of Japan

[73] Assignee: Toyo Jozo Kabushiki Kaisha, Shizuoka, Japan

[*] Notice: The portion of the term of this patent subsequent to Sep. 22, 2003 has been disclaimed.

[21] Appl. No.: 877,758

[22] Filed: Jun. 24, 1986

Related U.S. Application Data

[60] Division of Ser. No. 776,093, Sep. 16, 1985, Pat. No. 4,613,666, which is a continuation of Ser. No. 330,696, Dec. 14, 1981, abandoned.

[30] Foreign Application Priority Data

Dec. 19, 1980 [JP] Japan .................... 55-178825

[51] Int. Cl.$^4$ .................... C07D 473/30; A61K 31/52
[52] U.S. Cl. .................... 544/277; 544/276
[58] Field of Search ............ 544/277, 276; 514/261, 514/262, 263

[56] References Cited

U.S. PATENT DOCUMENTS

| | | | |
|---|---|---|---|
| 4,138,562 | 2/1979 | Vince | 544/277 |
| 4,423,218 | 12/1983 | Otani et al. | 544/277 |
| 4,613,666 | 9/1986 | Fukikawa et al. | 544/277 |

Primary Examiner—Nicholas S. Rizzo
Attorney, Agent, or Firm—Young & Thompson

[57] ABSTRACT

Neplanocin A derivatives of the formula

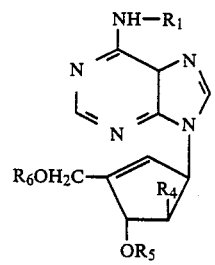

wherein $R_1$ is hydrogen or benzoyl, $R_4$ is hydrogen or halogen, hydroxy, acetoxy, acetylthio, amino or azide, $R_5$ is hydrogen or acetyl, and $R_6$ is hydrogen or acetyl. The compounds of the present invention have inhibitory action for the growth of L 5178 Y cells and have the same or superior activity as neplanocin A.

1 Claim, No Drawings

2'-(R)-SUBSTITUTED-2'-DEOXYNEPLANOCIN A DERIVATIVES

This appplication is a division of our copending application Ser. No. 776,093, filed Sept. 16, 1985, U.S. Pat. No. 4,613,666, which in turn is a continuation of our application Ser. No. 330,696, filed Dec. 14, 1981 and now abandoned.

This invention relates to novel neplanocin A derivatives. More particularly, the present invention relates to neplanocin A derivatives of the formula

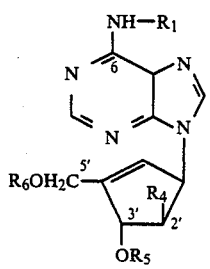

wherein $R_1$ is hydrogen or benzoyl, $R_4$ is hydrogen or halogen, hydroxy, acetoxy, acetylthio, amino or azide, $R_5$ is hydrogen or acetyl, and $R_6$ is hydrogen or acetyl.

Neplanocin A, originally designated as antibiotic A 11079-B1b, is an antibiotic produced by *Ampullariella* sp. A 11079 FERM-P No. 4494 having antitumor activity and inhibitory action for plant pathogenic fungi (U.S. application Ser. No. 18,790, filed Mar. 8, 1979 and its continuing application filed Nov. 3, 1980 and Japan patent Open. No. 54-154792). According to the results of instrumental analysis and the similarity of this antibiotic to aristeromycin [J. Chem. Soc. Chem. Comm., 852-853 (1967), Chem. Pharm. Bull., 20(5), 940-946 (1972)], the neplanocin is a nucleoside antibiotic-related substance, having a cyclopentene ring, of the formula

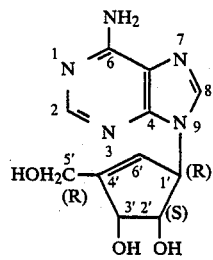

[refer to Current Chemotheraphy and Infectious Disease, 1558-1559 (1980)] and has an absolute configuration of 1' (R), 2' (R) and 3' (R). [Nucleic Acids Research, Symposium Series, No. 8, S 65-S 67 (1980)].

The compounds [I] of the present invention have an inhibitory action for the growth of L 5178 Y cells and have the same or superior activity as neplanocin A.

In the present invention, if the amine group at position $-6$ of adenine ring is not substituted, an acid addition salt can be made. Therefore, the pharmaceutically acceptable acid addition salts are within the scope of the present invention. Such a salt is a pharmacologically acceptable non-toxic salt, and can be an inorganic salt such as sulfate, hydrochloride or phosphate, or an organic salt such as acetate, propionate, maleate, tartrate, citrate or salt of an amino acid.

In a compound, substituent $R_4$ at position 2' has the absolute configuration (R), and contrary to the configuration of the hydroxy group at position 2' of neplanocin A as represented by formula [II], it has the arabino type configuration.

In the nomenclature of the above compound [I] and its intermediates, the positions of the substituents are designated according to the position number shown in formula [II].

A process for the production of compound [I] of the present invention is as follows:

(1) A compound [I] wherein $R_1$ is hydrogen or benzoyl, $R_5$ and $R_6$ are hydrogen and $R_4$ is acetoxy, i.e. a compound of the formula

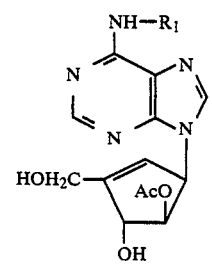

wherein $R_1$ has the same meaning as hereinabove and Ac is acetyl, can be synthesized by protecting the hydroxyl group at positions 3' and 5' of a compound of the formula

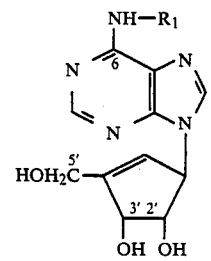

wherein $R_1$ has the same meaning as hereinabove, with 1,1,3,3,-tetraisopropyl disiloxane-1,3-di-yl to obtain a compound of the formula

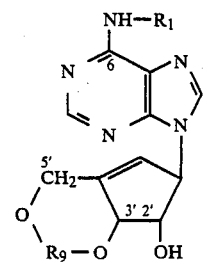

wherein $R_9$ is $-Si(i-Pro)_2-O-Si(i-Pro)_2-$, i-Pro is isopropyl and $R_1$ has the same meaning as hereinabove, trifluoromethansulfonylating the hydroxy group at position 2' of the said compound to obtain the intermediate of the formula

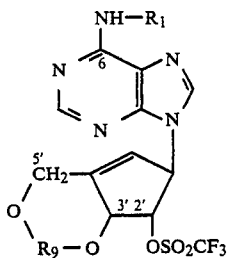

wherein $R_1$ and $R_5$ have the same meanings as hereinabove, reacting this intermediate with alkali metal acetate to obtain an intermediate of the formula

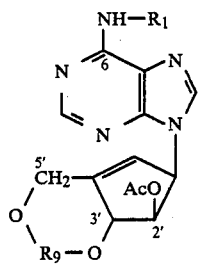

wherein $R_1$, Ac and $R_9$ have the same meanings hereinabove, and removing the 3′,5′-O-protective group by treating with tetrabutylammonium fluoride.

A starting material [2] wherein $R_1$ is benzoyl, i.e. $N^6$-benzoyl neplanocin A, is produced by reacting neplanocin A with a benzoylation reagent in the presence of a tertiary organic amine to obtain a benzoylated compound of the formula

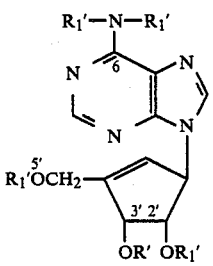

wherein $R_1'$ is benzoyl, and treating the thus-obtained compound with alkali hydroxide. An example of the benzoylation reagent is conventionally benzoyl chloride. Benzoylation can be performed in the presence of a tertiary organic amine such as pyridine, N-methylmorpholine or dimethylaniline. The benzyl groups, except the one at position $N^6$, are removed by treating compound [1] with alkali hydroxide.

The protection of the hydroxy groups at positions 3′ and 5′ of compound [2] can preferably be effected with 1,1,3,3-tetraisopropyl disiloxane-1,3-di-yl. The introduction of this protective group is described in J. Chem. Res., (1979), 24–25, 181–197. Other protective groups used in the field of saccharide and nucleic acid chemistry can be used.

The thus-obtained compound [3] can be isolated because it is stable in water due to the existing disiloxazinyl group in compound (3).

Trifluoromethane sulfonylation of the hydroxy group at position 2′ of compound [3] can be effected by reacting with a trifluoromethane sulfonylhalide such as trifluoromethane sulfonyl chloride in the presence of a tertiary organic amine such as triethylamine or pyridine in an organic solvent. 4-dimethylaminopyridine is preferably added for promotion of the reaction.

Compound [5] is obtained by reacting the thus-obtained compound [4] with an alkali metal acetate in an organic solvent such as hexamethylphosphoramide. Examples of alkali metal acetate are sodium acetate, potassium acetate and lithium acetate. The reaction proceeds at room temperature and requires no heat unless it proceeds too slowly.

Removal of the 3′,3′-O-protective group in compound [5] can easily be effected by treating with tetrabutylammonium fluoride in an organic solvent. Examples of organic solvents are tetrahydrofurance and dioxane. The reaction proceeds at room temperature in a short time.

Isolation and purification of the compound [A1] can be effected as hereinafter explained.

(2) A compound wherein $R_1$ is hydrogen or benzoyl, $R_4$ is acetylthio, $R_5$ and $R_6$ are hydrogen, i.e. a compound of the formula

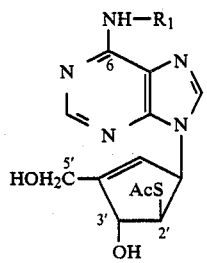

wherein Ac is acetyl, is produced by reacting compound [4] with an alkali metal thioacetate to obtain a compound of the formula

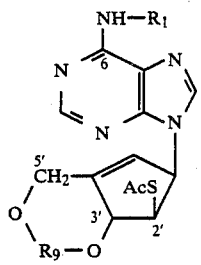

wherein $R_9$ is -Si(i-Pro)$_2$-O-Si(i-Pro)$_2$-, iPro is isopropyl and $R_1$ and Ac have the same meanings as hereinbefore, and removing the 3′,5′-O-protective group by tetrabutylammonium fluoride.

Examples of alkali metal thioacetate are sodium thioacetate, potassium thioacetate and lithium thioacetate. The reaction of compound [4] and an alkali metal thioacetate, and the removal of the 3′,5′-O-protective group in compound [6], are performed by the same procedure as in (1) above.

The thus-obtained compound [A2] can be isolated and purified as explained hereinafter.

(3) A compound, wherein $R_1$ is hydrogen or benzoyl, $R_4$ is halogen, $R_5$ and $R_6$ are hydrogen, i.e. a compound of the formula

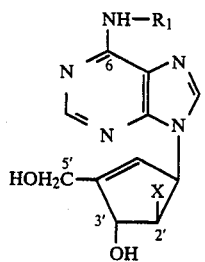

wherein $R_1$ is hydrogen or benzoyl and X is halogen, is produced by reacting compound [4] with alkali halogenide of the formula

MX wherein X is halogen and M is a reactive alkali metal atom, in an organic solvent to obtain a compound of the formula

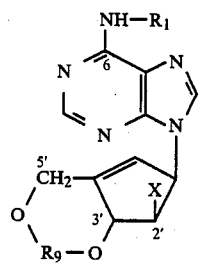

wherein $R_9$ is -Si(i-Pro)$_2$-O-Si(i-Pro)$_2$-, i-Pro is isopropyl, and $R_1$ and X have the same meanings as hereinbefore, and removing the 3',5'-O-protective group with tetrabutyl ammonium fluoride.

Examples of alkali halide as halogenating reagent having reactivity for 2'-halogenation of compound [4] are LiF, LiCl, LiBr, LiI and NaI.

An example of an organic solvent for the above halogenation is hexamethylphosphoramide. The halogenation can be conducted at room temperature and hence it is not necessary to heat unless the reaction rate is too slow.

The removal of the 3',5'-O-protective group in compound [7] can be effected by the same process as explained in (1) hereinbefore.

Compound [A3] can be purified by the process hereinafter explained.

(4) A compound wherein $R_1$ is hydrogen or benzoyl, $R_4$ is azide and $R_5$ and $R_6$ are hydrogen, i.e. a compound of the formula

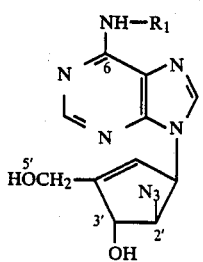

wherein $R_1$ is hydrogen or benzoyl, is produced by reacting compound [4] with an alkali metal azide to obtain a compound of the formula

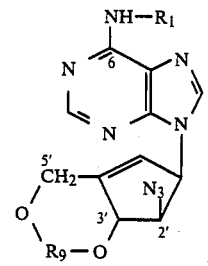

wherein $R_9$ is -Si(i-Pro)$_2$-O-Si(i-Pro)$_2$-, i-Pro is isopropyl and $R_1$ has the same meaning as hereinbefore, and removing the 3',5'-O-protective group with tetrabutyl ammonium fluoride.

Examples of alkali metal azide are lithium azide, potassium azide and sodium azide. The preferred organic solvent in the azidation reaction is hexamethylphosphoramide. The azidation reaction proceeds at room temperature and hence it is not necessary to heat unless the reaction rate is too slow.

Removal of the 3',5'-O-protective group from compound [8] can be performed by the same process as explained in (1) hereinbefore.

The thus-obtained compound can be purified as hereinafter explained.

(5) A compound [I], wherein $R_1$ is hydrogen or benzoyl, $R_4$ is amino, and $R_5$ and $R_6$ are hydrogen, i.e. a compound of the formula

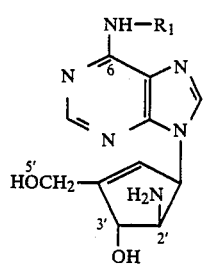

wherein $R_1$ is hydrogen or benzoyl, is produced by reducing compound [A4].

The reduction of the azide group to an amino group is performed by bubbling hydrogen sulfide in pyridine. The reaction proceeds at room temperature.

The thus-obtained compound [A5] can be purified as hereinafter explained.

(6) A compound [I], wherein $R_1$ is hydrogen or benzoyl, $R_2$ is hydrogen, and $R_5$ and $R_6$ are hydrogen, i.e. a compound of the formula

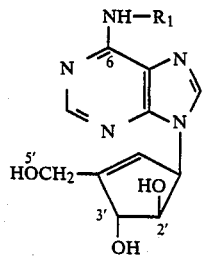

wherein $R_1$ is hydrogen or benzoyl, can be obtained by de-acetylation of compound [A1].

Deacetylation can be performed by treating with ammonia or an alkali metal alcoholate in methanol.

The 2'-acetoxy group together with the $N^6$-benzoyl group are removed by treating with an alkali metal alcoholate such as sodium methylate.

The product [A6] can be purified by the method hereinafter explained.

(7) A compound [I], wherein $R_1$ is hydrogen or benzoyl, and $R_4$, $R_5$ and $R_6$ are hydrogen, i.e. a compound of the formula

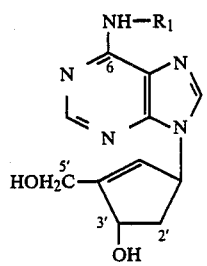

wherein $R_1$ is hydrogen or benzoyl, is produced by treating a compound [7] hereinbefore or a compound of the formula

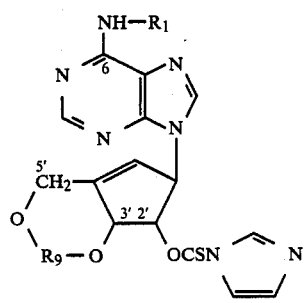

wherein $R_1$ is hydrogen or benzoyl, $R_9$ is $OSi(i-Pro)_2-O-Si(i-Pro)_2-$ and i-Pro is isopropyl, with hydrogenated tin tributylate in an organic solvent to obtain a compound of the formula

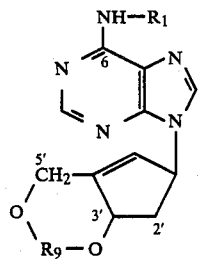

wherein $R_1$ and $R_9$ have the same meanings as hereinbefore, and removing the 3',5'-O-protective group by treating with tetrabutyl ammonium fluoride.

The starting material [9] can be prepared by reacting compound [3] with N,N'-thiocarbonyldiimidazole in an organic solvent such as chloroform, methylene chloride or ethylene chloride. The reaction proceeds at room temperature. The reaction of the above compound [7] or [9] and hydrogenated tin tributylate is performed in an organic solvent such as benzene or toluene under heating. In the above reaction, azo bis-isobutylnitrile is preferably added as a catalyst and the reaction proceeds under an atmosphere of argon.

The 3',5'-O-protective group in the intermediate [10] obtained by the above reaction is removed by the same method as explained hereinbefore (1).

The thus-obtained compound [A7] can be purified by the method hereinbefore explained.

(8) A compound [I], wherein $R_1$ is hydrogen or benzoyl, $R_4$ is acetoxy or halogen, and $R_5$ and $R_6$ are acetyl, i.e. a compound of the formula

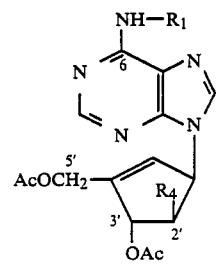

wherein $R_1$ is hydrogen or benzoyl, and $R_4$ is acetoxy or halogen, is produced by acetylating compound [A1] or [A3].

The acetylation reaction is conducted by reacting with acetic anhydride in pyridine at room temperature. The resulting compound [A8] is purified by the method hereinbefore explained.

The compound [I] hereinabove and its intermediates can be isolated and purified by vacuum concentration, extraction, crystallization or chromatography using silica-gel, active carbon, cellulose or Sephadex.

In case compound [I] is a basic substance, for example compound [A5] can be isolated as an acid addition salt thereof. In that case, the base is neutralized with acid, and the acid addition salt thereof is crystallized or subjected to column chromatography to purify the product.

The growth-inhibitory activities of compound [I] of the present invention on L 5178 Y cells are shown below.

(1) Test method:

A test sample (0.3 ml) dissolved in a medium [bovine serum (10%) in Fischer's medium] is added to a mouse lymphoma L 5178 Y cells suspension (2.7 ml, $5 \times 10^4$/ml cells), and the mixture is incubated at 37° C. for 22 hours. Cell-growth is observed by checking the color change of phenol red in the medium. The minimum inhibitory concentration (MIC) of the substance on cell growth is defined by observing apparent growth inhibition as compared with that of control.

(2) Test results:

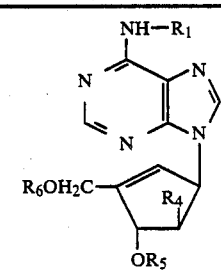

| $R_1$ | $R_4$ | $R_5$ | $R_6$ | $\gamma$/ml |
|---|---|---|---|---|
| H | H | H | H | 4 |

-continued

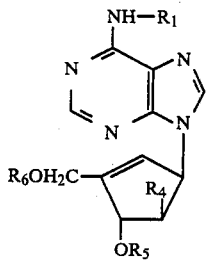

| R₁ | R₄ | R₅ | R₆ | γ/ml |
|---|---|---|---|---|
| H | Cl | H | H | 20 |
| H | Br | H | H | 4 |
| H | I | H | H | 4 |
| H | N₃ | H | H | 100 |
| H | NH₂ | H | H | 4 |
| H | Cl | Ac | Ac | 100 |
| COPh | I | H | H | 100 |

The following examples illustrates the process of manufacture of compound of the present invention. In these examples, the carriers and developers on thin layer chromatopgraphy (TLC) are, if not specified, as follows:

Carrier: silica-gel (Merck, Art. 5729)
Developer:
1. Chloroform-methanol (1:1)
2. Chloroform-methanol (5:1)
3. Chloroform-methanol (10:1)
4. Chloroform-methanol (20:1)
5. Chloroform-methanol (40:1)
6. Benzene-ethyl acetate (1:1)
7. Chloroform-ethanol (10:1)

Carrier: silica-gel (merck, Art. 5715)
Developer:
8. Propyl alcohol-water-conc. aqueous ammonia (6:3:1)
9. Acetone-water (10:3)

EXAMPLE 1

N$^6$-benzoyl neplanocin A (1) A methylene chloride solution (5 ml) of benzoyl chloride (0.78 ml) was added dropwise with stirring with ice cooling to neplanocin A (263 mg) dissolved in anhydrous pyridine (5 ml). The temperature was gradually increased to room temperature and the mixture was stirred for 8 hours. The reaction mixture was poured into ice water and extracted three times with chloroform. The combined extracts were washed with water, passed through Whatman 1PS filter paper and concentrated in vacuo. The residue was purified by silica gel column chromatography using chloroform to obtain a powder of N$^6$,N$^6$,2'-O,3'-O,5'-O-pentabenzoyl neplanocin A (587 mg).

NMR: δppm (CDCl₃) 5.16 (2H, J≃O, H-5'), 5.98 (1H, q., H-2'), 6.06 (1H, J≃0, H-1'), 6.31 (1H, J≃O, H-6'), 6.50 (1H, d., H-3'), 7.2–8.1 (25H, m., phenyl proton), 8.15 (1H, S., H-2), 8.56 (1H, S., H-8)

(2) The product (500 mg) obtained in the above (1) was dissolved in ethanol (3 ml) and pyridine (1.5 ml). A mixture of 2N-sodium hydroxide (3 ml) and ethanol (3 ml) was added at once and the mixture was stirred for 5 minutes. The reaction mixture was neutralized by adding Dowex 50 (pyridinium type), and the resulting material was filtered and washed with ethanol followed by pyridine. The filtrate and washings were collected, concentrated in vacuo and methanol was added thereto to obtain N$^6$-benzoyl neplanocin A crystals (187 mg).
m.p.: 180°–183° C.

NMR: δppm (DMSO-d₆) 4.16 (2H, m., H-5'), 4.36 (1H, q.), H-2'), 4.44 (1H, t., H-3'), 4.94 (1H, t., 5'-OH, exchanged by D₂O), 5.02 (1Hd, OH, exchanged by D₂O), 5.21 (1Hd, OH, exchanged by D₂O), 5.50 (1H, m., H-1'), 5.76 (1H, J≃O, H-6'), 7.4–8.1 (5H, m., phenyl proton), 8.40 (1H, S., H-2), 8.70 (1H, S., H-8), 10.38 (1H S., NH, exchanged by D₂O)

EXAMPLE 2

3',5'-O-(1,1,3,3-tetraisopropyl disiloxane-1,3-di-yl) neplanocin A

Neplanocin A (236 mg) and imidazole (300 mg) were dissolved in dimethylformamide (3 ml). 1,3-dichloro-1,1,3,3-tetraisopropyl disiloxane (350 mg) was added thereto and the mixture was stirred at room temperature for 40 minutes. Water (20 ml) was added to the reaction mixture which was then ice cooled to precipitate the oily material which was decanted and dissolved in chloroform, then washed with water. The organic layer was passed through Whatman 1PS filter paper and concentrated in vacuo. The residue was purified by silica gel column chromatography using chloroform-ethanol (30:1). Fractions showing Rf₃=0.50 were collected and dried in vacuo to obtain 3',5'-O-(1,1,3,3-tetraisopropyl disiloxane-1,3-di-yl) neplanocin A (212 mg).
m.p.: 185°–186° C.

Elementary analysis [$C_{23}H_{39}O_4N_5Si_2$]:

| | C % | H % | N % |
|---|---|---|---|
| Found: | 54.47 | 7.79 | 13.81 |
| Calculated: | 54.62 | 7.77 | 13.85 |

NMR: δppm (CDCl₃) 1.1 (28H, isopropyl), 3.59 (1H, d., OH-2', exchanged by D₂O), 4.32 (1H, Sextet, H-2', d.d by D₂O), 4.52 (2H, slightly broad, H-5'), 5.32 (1H, d., H-3'), 5.50 (1H, slightly broad, H-1'), 5.60 (2H, slightly broad, NH₂-6, exchanged by D₂O), 5.83 (1H, H-6'), 7.76 (1H, S., H-2), 8.36 (1H, S., H-8).

Mass: 505 (M+), 462 (M+ −43), 136, 135.

EXAMPLE 3

N$^6$-benzoyl-3',5'-O-(1,1,3,3-tetraisopropyl disiloxane-1, 3-di-yl) neplanocin A N$^6$-benzoyl neplanocin A (926 mg) and imidazole (755 mg) were dissolved in dry dimethylformamide (15 ml). 1,3-dichloro-1,1,3,3-tetraisopropyl disiloxane (870 mg) was added thereto and the mixture was stirred at room temperature for 10 minutes. Water was added with ice cooling, and the mixture was concentrated in vacuo and the residue was extracted with chloroform. The organic layer was washed with water, passed through Whatman 1PS filter paper and concentrated in vacuo. The residue was purified by Florisil column chromatography using chloroform-methanol (30-20:1) (1.25 g, yield: 82%).

NMR: δppm (CDCl₃) 1.1 (28H, isopropyl), 3.48 (1H, d., OH-2', exchanged by D₂O), 4.34 (1H, Sextet, H-2', d.d. by D₂O), 4.50 (2H, slightly broad, H-5'), 5.34 (1H, d., H-3'), 5.55 (1H, slightly broad, H-1 ), 5.82 (1H, h-6'), 7.4–8.1 (6H, phenyl proton and H-2 or H-8), 8.78 (1H, S., H-8 or H-2), 8.96 (1H, broad, NH, exchanged by D₂O).

UV: $\lambda_{max}^{MeOH}$=282 nm

Mass: 609 (M+), 566 (M+−43)

EXAMPLE 4

2′-O-trifluoromethanesulfonyl-3′,5′-O-(1,1,3,3-tetraisopropyl disiloxane-1,3-di-yl) neplanocin A 4-dimethylaminopyridine (570 mg) and triethylamine (0.65 ml were added to 3′,5′-O-(1,1,3,3-tetraisopropyl disiloxane-1,3-di-yl) neplanocin A (2.36 g) dissolved in dry pyridine (15 ml). Trifluoromethanesulfonylchloride (0.5 ml) was added dropwise thereto while stirring with ice cooling. The temperature was gradually increased to room temperature. The reaction mixture was stirred for 30 minutes, poured into ice water, then extracted several times with chloroform. The extract was washed with water, passed through Whatman 1PS filter paper and concentrated in vacuo. The residue was purified by silica gel column chromatography using chloroform-ethanol (30:1). Fractions showing $Rf_3=0.16$ were collected and concentrated in vacuo to obtain porous 2′-O-tri-fluoromethanesulfonyl-3′,5′-O-(1,1,3,3-tetraisopropyl disiloxane-1,3-di-yl) neplanocin A (2.1 g, yield: 70.5%).

NMR: δppm (CDCl$_3$) 1.1 (28H, isopropyl), 4.51 (2H, slightly broad, H-5′), 5.38 (1H, d.d., H-2′), 5.58 (3H, 6-NH$_2$ and H-3′, d. by D$_2$O, h-3′), 5.69 (1H, m., H-1′), 5.94 (1H, J≃O, H-6′), 7.73 (1H, S., H-2), 8.32 (1H, S., H-8)

UV: $\lambda_{max}^{MeOH}=262$ nm

Mass: 594 (M+−43), 495, 477, 367, 253, 235, 135.

EXAMPLE 5

N$^6$-benzoyl-2′-O-trifluoromethanesulfonyl-3′,5′-O-(1,1,3,3-tetraisopropyl disiloxane-1,3-di-yl) neplanocin A Triethylamine (0.04 ml) and 4-dimethylaminopyridine (10 mg) were added to N$^6$-benzoyl-3′,5′-0-(tetraisopropyl disil(oxane-1,3-di-yl) neplanocin A (52 mg) dissolved in pyridine (1 ml). Trifluoromethanesulfonylchloride (0.01 ml) was added dropwise with ice cooling. The temperature was gradually increased to room temperature. The reaction mixture was stirred for 3 hours, poured into ice water and then extracted with chloroform. The organic layer was passed through Whatman 1PS filter paper and concentrated in vacuo. The residue was purified by silica gel column chromatography using chloroform-methanol (30:1) to obtain N$^6$-benzoyl-2′-O-trifluoromethanesulfonyl-3′,5′-0-(1,1,3,3tetraisopropyl disiloxane-1,3-di-yl) neplanocin A (48 mg).

NMR: δppm (CDCl$_3$) 1.1 (28H, isopropyl), 4.52 (1H, d.d., H-2′), 5.58 (1H, d., H-3′), 5.76 (1H, slightly broad, H-1′), 5.86 (1H, h-6′), 7.4-8.1 (6H, phenyl proton and H-2 or H-8), 8.75 (1H, S., H-8 or H-2), 9.00 (1H, broad, NH).

EXAMPLE 6

2′-(R)-acetoxy-2′-deoxy neplanocin A (1) Sodium acetate (163 mg) was added to 2′-O-tri-fluoro-methanesulfonyl-3′,5′-O-(1,1,3,3-tetraisopropyl disiloxane-1,3-di-yl) neplanocin A (1.06 g) dissolved in hexamethylphosphoramide (10 ml), and the mixture was stirred at room temperature for 1.5 days. The reaction mixture was poured into ice water, extracted with chloroform, the organic layer was washed with water, passed through Whatman 1PS filter paper and concentrated in vacuo. The residue was purified by silica gel column chromatography using chloroform-ethanol (30:1). Fractions showing $Rf_3=0.36$ were collected and dried in vacuo to obtain 2′-(R)-acetoxy-2′-deoxy-3′,5′-O-(1,1,3,3-tetraisopropyl disiloxane-1,3-di-yl) neplanocin A (270 mg).

NMR: δppm (CDCl$_3$) 1.1 (28 H, isopropyl), 1.61 (3H, S., OCOCH$_3$), 4.45 (2H, slightly broad, H-5′), 5.32 (lH, t., H-3′), 5.44 (lH d.d., H-2 ), 5.6–6.0 (4H, NH$_2$ and H-6′, H-1′,2H by D$_2$O), 7.69 (1H, S., H-2), 8.34 (1H, S., H-8).

UV: $\lambda_{max}^{MeOH}=261$ nm

Mass: 547 (M$^{30}$), 504 (M+−43), 352, 228, 136, 135.

(2) The product obtained in the above (1) (270 mg) was dissolved in anhydrous tetrahydrofuran (4 ml). Tetrabutylammonium fluoride (140 mg) was added thereto while stirring at room temperature. Immediately oily material was precipitated and stirring was continued for a further 10 minutes. The reaction mixture was concentrated in vacuo and the residue was recrystallized from ethanol to obtain 2′-(R)-acetoxy-2′-deoxy neplanocin A (120 mg, yield: 80%).

m.p.: 195°–197° C.

Elementary analysis [C$_{13}$H$_{15}$O$_4$N$_5$]:

|  | C % | H % | N % |
|---|---|---|---|
| Found: | 51.12 | 4.98 | 22.74 |
| Calculated: | 51.14 | 4.95 | 22.94 |

NMR: δppm (DMSO-d$_6$) 1.52 (3H, S., OCOCH$_3$), 4.17 (2H, slightly broad, H-5′), 4.82 (1H, slightly broad, H-3′, d by D$_2$0), 4.97 (1H, t., OH-5′, exchanged by D$_2$O), 5.18 (1H, d.d., H-2′), 5.55 (1H, d., OH-3′, exchanged by D$_2$O), 5.64 (1H, d.d., H-1′), 5.80 (1H, d., H-6′), 7.18 (2H, broad, S., NH$_2$, exchanged by D$_2$O), 7.82 (1H, S., H-2), 8.11 (1H, S., H-8).

UV: $\lambda_{max}^{MeOH}=262$ nm

Mass: 306 (M+−1), 304, 287, 262, 245, 136, 135.

CD: $[\theta]-11,900$ (252 nm, H$_2$O)

EXAMPLE 7

2′-(R)-hydroxy-2′-deoxy neplanocin A

Methanolic ammonia [ammonia-gas-saturated methanol (50 ml) at 0° C. ] was added to 2′-(R)-acetoxy-2′-deoxy neplanocin A (74 mg) and the mixture was stirred at room temperature for 3.5 hours. The reaction mixture was dried in vacuo. The residue was recrystallized from aqueous ethanol to obtain 2′-(R)-hydroxy-2′ -deoxy neplanocin A (185 mg, yield: 92%).

m.p.: 239°–240.5° C.

Elementary analysis [C$_{11}$H$_{13}$O$_3$N$_5$.⅓H$_2$O]:

|  | C % | H % | N % |
|---|---|---|---|
| Found: | 49.01 | 5.01 | 25.97 |
| Calculated: | 49.13 | 5.00 | 26.04 |

NMR: δppm (DMSO-d$_6$) 4.14 (3H, m., H-5′ and H-2′), 4.56 (1H, t., H-3′, d by D$_2$O), 4.86 (1H, t., OH-5′, exchanged by D$_2$O), 5.18, 5.22 (each 1H, each d., OH-2′ and OH-3′, exchanged by D$_2$O), 5.52 (1H, d.d., H-1′), 5.72 (1H, J≃O, H-6′), 7.10 (2H, slightly broad, S., NH$_2$), 7.78 (1H, S., H-2), 8.12 (lH, S., H-8)

UV: $\lambda_{max}^{H2O}=262$ nm

Mass: 264 (M++1), 263 (M+), 245, 216, 186, 136, 135.

TLC: $Rf_2=0.10$, Rf=0.46 [ethanol+boric acid in aqueous ammonium acetate (0.5 M) (5:2), silica gel plate]

EXAMPLE 8

N6-benzoyl-2'-(R)-acetoxy-2'-deoxy neplanocin A (1) N6-benzoyl-2'-trifluoromethanesulfonyl-3',5'-O-(1,1,3,3-tetraisopropyl disiloxane-1,3-di-yl) neplanocin A (30 mg) was dissolved in hexamethylphosphoramide (0.5 ml). Sodium acetate (3.7 mg) was added thereto and the mixture was stirred at room temperature for 6.5 hours. Further sodium acetate (3 mg) was added thereto and the mixture was stirred for 12 hours. The reaction mixture was extracted with chloroform and washed with water. The organic layer was concentrated in vacuo, and purified by silica gel TLC using benzene-ethyl acetate (1:1). The band showing $Rf_6=0.21$ was collected, extracted with chloroform-methanol (1:1) and dried in vacuo to obtain N6-benzoyl-2'-(R)-acetoxy-2'-deoxy-3',5'-O-(1,1,3,3-tetraisopropyl disiloxane-1,3-di-yl) neplanocin A (10 mg).

NMR: $\delta$ppm (DMSO-$d_6$) 1.1 (28H, isopropyl), 1.60 (3H, S., PCPCH$_3$), 4.46 (2H, slightly broad, H-5'), 5.3–5.5 (2H, m., H-2' and H-3'), 5.87 (2H, H-6' and H-1'), 7.4–8.1 (6H, phenyl proton and H-2 or H-8), 8.76 (1H, S., H-8 or H-2), 9.04 (1H, broad, NH)

Mass: 651 (M+), 608, 622, 591, 504, 369, 352, 105.

(2) The product obtained in the above (1) (45 mg) was dissolved in anhydrous tetrahydrofuran (1 ml). Tetrabutylammonium (21 mg) was added thereto and the mixture was stirred at room temperature for 10 minutes. The reaction mixture was concentrated in vacuo and the residue was recrystallized from ethanol to obtain N6-benzoyl-2'-(R)-acetoxy-2'-deoxy neplanocin A (15 mg).

m.p.: 205°–207° C.

NMR: $\delta$ppm (DMSO-$d_6$) 1.52 (3H, S., OCOCH$_3$), 4.02 (2H, m., H-5'), 4.88 (1H, d.d., H-3', d. by D$_2$O), 5.03 (1H, t., OH-5', exchanged by D$_2$O), 5.26 (1H, d.d., H-2'), 5.62 (1H, d., OH-3', exchanged by D$_2$O), 5.87 (2H, H-6' and H-1'), 7.4–8.1 (5H, m., phenyl proton), 8.22 (1H, S., H-2 or H-8), 8.71 (1H, S., H-8 or H-2), 11.13 (1H, broad, NH, exchanged by D$_2$O)

Mass: 409 (M+), 408, 349, 304, 228, 105.

UV: $\lambda_{max}^{MeOH}=281$ nm

Elementary analysis [$C_{20}H_{19}N_5O_5 \cdot \frac{1}{2}H_2O$]:

|  | C % | H % | N % |
|---|---|---|---|
| Found: | 57.55 | 4.78 | 16.70 |
| Calculated: | 57.41 | 4.82 | 16.74 |

EXAMPLE 9

2'-(R)-hydroxy-2'-deoxy neplanocin A

N6-benzoyl-2'-(R)-acetoxy-2'-deoxy neplanocin A (5 mg) was suspended in methanol (2 ml). The suspension was adjusted to pH 10 by adding a methanol solution of sodium methoxide. A homogeneous solution was obtained. After checking the disappearance of the starting material, the solution was neutralized by Dowex 50 (H+). The resin was washed with water, eluted with aqueous ammonia-methanol and concentrated in vacuo. The residue was charged on a TLC plate and eveloped by benzene-ethyl acetate (1:1). The band showing $Rf_2=0.10$ was collected, extracted with chloroform-methanol (1:1) and dried in vacuo to obtain 2'-(R)-hydroxy-2'-deoxy neplanocin A. The thus-obtained product was identical with the compound obtained in Example 7, according to instrumental analysis.

EXAMPLE 10

2'-(R)-azide-2'-deoxyneplanocin A (1)

2'-O-trifluoromethanesulfonyl-3',5'-O-(1,1,3,3-tetraisopropyl disiloxane-1,3-di-yl) neplanocin A (63.7 mg) obtained in Example 15 was dissolved in hexamethylphosphoramide (0.5 ml). Lithium azide (8.5 mg) was added thereto and the mixture was stirred at room temperature for 10 hours. The reaction mixture was extracted with chloroform, washed with water and concentrated in vacuo. The residue was charged on a silica gel TLC plate and developed by benzene-ethyl acetate (1:1). The band showin $Rf_6=0.10$ was collected, extracted with chloroform-methanol (1:1) and dried in vacuo. The product was recrystallized from methanol to obtain 2'-(R)-azide-2'-deoxy-3',5'-O-(1,1,3,3-tetraisopropyl disiloxane-1,3-di-yl) neplanocin A (43 mg, yield: 81%).

m.p.: 189°–191° C. (white needle crystals)

Elementary analysis [$C_{23}H_{38}O_3N_8Si_2$]:

|  | C % | H % | N % |
|---|---|---|---|
| Found: | 51.81 | 7.19 | 20.95 |
| Calculated: | 52.04 | 7.22 | 21.11 |

NMR: $\delta$ppm (CDCl$_3$) 1.1 (28H, isopropyl), 4.27 (1H, d.d., H-2'), 4.44 (2H, S., H-5), 5.06 (1H, d., H-1'), 5.84 (1H, J$\simeq$0, H-6'), 7.64 (1H, S., H-2), 8.38 (1H, S., H-8).

UV: $\lambda_{max}^{MeOH}=262$ nm

Mass: 530 (M+), 488 (M+ 42), 487 (M+ −43), 432, 324.

IR: $\nu$N$_3$ (KBr) 2110 cm$^{-1}$.

(2) 2'-(R)-azide-2'-deoxy-3',5'-O-(1,1,3,3-tetraisopropyl disiloxane-1,3-di-yl) neplanocin A (250 mg) obtained in the above (1) was dissolved in anhydrous tetrahydrofuran (5 ml). Tetrabutylammonium fluoride (135 mg) was added dropwise with stirring at room temperature for 5 minutes. The reaction mixture was concentrated in vacuo. The residue was recrystallized from ethanol to obtain 2'-(R)-azide-2'-deoxy neplanocin A (11 g mg, yield: 82%).

m.p.: 231°–233° C. (decomp.)

Elementary analysis [$C_{11}H_{12}O_2N_8$]:

|  | C % | H % | N % |
|---|---|---|---|
| Found: | 45.86 | 4.25 | 38.66 |
| Calculated: | 45.83 | 4.20 | 38.77 |

NMR: $\delta$ppm (DMSO-$d_6$) 4.15 (2H, slightly broad, H-5'), 4.27 (1H, d.d., H-2'), 4.81 (1H, t., H-3'), 4.95 (1H, t., OH-5', exchanged by D$_2$O), 5.64 (1H, d.d., H-1'), 5.75 (1H, d., OH-3', exchanged by D$_2$O), 5.77 (1H, J=O, H-6 ), 7.21 (2H, broad, S., NH$_2$, exchanged by D$_2$O), 7.88 (1H, S., H-2), 8.15 (1H, S., H-8).

UV: $\lambda_{max}^{H_2O}=262$ nm.

Mass: 289 (M++1), 288 (M+), 246 (M+ −42), 186, 136, 135.

IR: $\nu$N$_3$ (KBr) 2115 cm$^{-1}$

CD: [$\theta$] −19,900 (253 nm, H$_2$O)

EXAMPLE 11

2'-(R)-chloro-2'-deoxy neplanocin A

2'-O-trifluoromethanesulfonyl-3',5'-O-(1,1,3,3-tetraisopropyl disiloxane-1,3-di-yl) neplanocin A (500 mg)

obtained in Example 4 was dissolved in hexamethylphosphoramide (5 ml). Lithium chloride (43 mg) was added thereto and the mixture was stirred at room temperature for 20 hours. The reaction mixture was poured into ice water and extracted with chloroform. The organic layer was washed with water, passed through Whatman 1PS filter paper, then concentrated in vacuo. The residue was charged on a silica gel TLC plate and developed by chloroform-ethanol (15:1). The band showing $Rf_3=0.51$ was collected, extracted with chloroform-methanol (1:1) and dried in vacuo to obtain 2'-(R)-chloro-2'-deoxy-3',5'-O-(1,1,3,3-tetraisopropyl disiloxane-1,3-di-yl ) neplanocin A. The product was dissolved in anhydrous tetrahydrofuran, and tetrabutylammonium fluoride was added thereto while stirring at room temperature to remove the protective silyl group. The reaction mixture was concentrated in vacuo. The residue was charged on a silica gel TLC plate, and developed by chloroform-methanol (5:1). The band showing $Rf_2=0.14$ was collected, extracted with chloroform-methanol (1:1) and concentrated in vacuo. The residue was recrystallized to obtain 2'-(R)-chloro-2'-deoxy neplanocin A (120 mg, yield: 55%).

m.p.: 233°-235° C. (decomp.)

Elementary analysis $[C_{11}H_{12}O_2N_5Cl]$:

|  | C % | H % | N % | Cl % |
|---|---|---|---|---|
| Found: | 46.88 | 4.32 | 24.79 | 12.51 |
| Calculated: | 46.90 | 4.29 | 24.86 | 12.59 |

NMR: δppm (DMSO-$d_6$) 4.16 (2H, slightly broad, H-5'), 4.54 (1H, d.d., H-2'), 4.91 (1H, t., H-3'), 5.00 (1H, t., OH-5', exchanged by $D_2O$), 5.74 (1H, d.d., H-1'), 5.85 (1H, d., OH-3', exchanged by $D_2O$), 5.86 (1H, J O, H-6'), 7.21 (2H, broad, S., $NH_2$, exchanged by $D_2O$), 7.96 (1H, S., H-2), 8.14 (1H, S., H-8).

UV: $\lambda_{max}^{H2O}=262$ nm

Mass: 284, 282 (M++1), 283, 281 (M+), 136, 135.

CD: $[\theta]-10,800$ (252 nm. $H_2O$)

EXAMPLE 12

2'-(R)-chloro-2'-deoxy-3'-O, 5'-O-diacetyl neplanocin A

Acetic anhydride (0.02 ml) was added to 2'-(R)-chloro-2'-deoxy neplanocin A (30 mg) dissolved n anhydrous pyridine (1 ml) and the mixture was stirred at room temperature for 8 hours. The reaction mixture was concentrated in vacuo. The residue was recrystallized from ethanol to obtain 2'-(R)-chloro-2'-deoxy-3'-O, 5-O-diacetyl neplanocin A (32 mg, yield: 82%).

m.p.: 179°-181° C.

TLC: $Rf_2=0.64$

NMR: δppm (CDCl$_3$) 2.14, 2.18 (each 3H, each S., OCOCH$_3$X$_3$), 4.72 (1H, d.d., H-2'), 4.78 (2H, S., H-5), 5.68 (2H, broad, S., $NH_2$, exchanged by $D_2O$), 6.0-6.1 (2H, H-1' and H-3'), 6.13 (1H, J), H-6'), 7.78 (1H, S., H-2), 8.37 (1H, S., H-8)

UV: $\lambda_{max}^{MeOH}=262$ nm

Mass: 368, 366 (M+1), 367, 365 (M+), 330, 288, 136, 135.

EXAMPLE 13 p 2'-(R)-bromo-2'-deoxy neplanocin A (1) 2'-trifluoromethanesulfonyl-3',5'-O-(1,1,3,3-tetraisopropyl disiloxane-1,3-di-yl) neplanocin A (500 mg) was dissolved in hexamethylphosphoramide (5 ml). Lithium bromide (70 mg) (anhydride obtained by heating the commercially available hydrated product) was added thereto and the mixture was stirred at room temperature for 2.5 hours. The reaction mixture was poured into ice water. The precipitated crystals were filtered, washed with water and dried in vacuo. Recrystallization was effected from cyclohexane to obtain 2'-(R)-bromo-2'-deoxy-3',5'-O-(1,1,3,3-tetraisopropyl disiloxane-1,3-di-yl) neplanocin A (440 mg).

m.p.: 175°-178° C.

Elementary analysis $[C_{23}H_{38}O_3N_5Si_2Br]$:

|  | C % | H % | N % | Br % |
|---|---|---|---|---|
| Found: | 48.56 | 6.77 | 12.27 | 14.13 |
| Calculated: | 48.58 | 6.74 | 12.32 | 14.05 |

NMR: δppm (CDCl$_3$) 1.1 (28H, isopropyl), 4.46 (2H, S., H-5'), 4.59 (1H, d.d., H-2'), 5.34 (1H, d., H-3'), 5.56 (2H, broad, S., $NH_2$, exchanged by $D_2O$), 5.78 (1H, d.d., H-1'), 5.90 (1H, J O, H-6'), 7.69 (1H, S., H-2), 8.38 (1H, S., H-8).

UV: $\lambda_{max}^{MeOH}=262$ nm

Mass: 569, 567 (M+), 526, 524, 488, 444, 353, 311.

CD: $[\theta]-15,300$ (252 nm, MeOH)

(2) The product (200 mg) obtained in the above (1) was dissolved in anhydrous tetrahydrofuran (5 ml). Tetra-n-butylammonium fluoride (100 mg) was added thereto while stirring at room temperature for 5 minutes. The reaction mixture was concentrated in vacuo. The residue was charged on a TLC plate and developed by chloroform-methanol (5:1). The band showing $Rf_2=0.30$ was collected extracted with chloroformmethanol (1:1), dried in vacuo, then recrystallized from ethanol. 95 mg, yield: 83%).

m.p.: 224°-226° C. (decomp.)

Elementary analysis $[C_{11}H_{12}O_2N_5Br]$:

|  | C % | H % | N % | Br % |
|---|---|---|---|---|
| Found: | 40.57 | 3.63 | 21.26 | 24.24 |
| Calculated: | 40.50 | 3.71 | 21.47 | 24.50 |

NMR: δppm (DMSO-$d_6$) 4.17 (2H, slightly broad, H-5'), 4.60 (1H, d.d., H-2'), 4.93-5.06 (2H, H-3' and OH-5', 1H by $D_2O$), 5.70 (1H, d.d., H-1'), 5.84 (1H, d., OH-3'), exchanged by $D_2O$), 5.86 (1H, J≈O, H-6'), 7.20 (2H, broad, $NH_2$, exchanged by $D_2O$), 7.96 (1H, S., H-2), 8.14 (1H, S., H-8).

UV: $\lambda_{max}^{H2O}=262$ nm

Mass: 327, 325 (M+), 246, 228, 136, 135.

CD: $[\theta]-13,000$ (252 nm $H_2O$)

EXAMPLE 14

2'-(R)-iodo-2'-deoxy neplanocin A

In Example 13, lithium bromide was replaced by sodium iodide to obtain 2'-(R)-iodo-deoxy neplanocin A. Yield: 380 mg.

m.p.: 212°-215° C. (decomp.)

UV: $\lambda_{max}^{H2O}=262$ nm

EXAMPLE 15

$N^6$-benzoyl-2'-(R)-iodo-2'-deoxy neplanocin A (1) The compound (50 mg) obtained in Example 5 and lithium iodide (15 mg) were dissolved in hexamethylphosphoramide (1 ml) and the mixture was stirred at room temperature for 24 hours. The reaction mixture was dissolved in chloroform, washed with water, passed through Whatman 1PS filter paper and concentrated in vacuo. The residue was treated by TLC in the same way as in Example 25 to obtain $N^6$-benzoyl-2'-(R)-iodo-2'-deoxy-3',5'-O-(tetraisopropyl disiloxane-1,3-di-yl) neplanocin A (35 mg).

NMR: δppm (CDCl$_3$) 1.1 (28 H, isopropyl), 4.51 (2H, slightly broad, H-5'), 4.70 (1H, d.d., H-2'), 5.46 (1H, d., H-3'), 5.78 (1H, d.d., H-1'), 5.92 (1H, J≃O, H-6'), 7.4–8.1 (5H, m., phenyl proton), 7.88 (1H, S., H-2 or H-8), 8.83 (1H, S., H-8 or H-2), 8.98 (1H, broad, NH, exchanged by D$_2$O).

Mass: 676 (M+ −43), 477, 253, 240, 239, 238.

(2) The protective groups of the product obtained in the above (1) were removed by the same procedure as in Example 19-(2) to obtain $N^6$-benzoyl-2'-(R)-iodo-2'-deoxy neplanocin A.

NMR: δppm (DMSO-d$_6$) 4.21 (2H, slightly broad, H-5'), 4.66 (1H, d.d., H-2'), 5.02 (1H, t., OH-5'), exchanged by D$_2$O), 5.13 (1H, t., H-3'), 5.78 (1H, d.d, H-1'), 5.84 (1H, d., OH-3', exchanged by D$_2$O), 5.90 (1H, J≃O, H-6'), 7.5–8.1 (5H, m., phenyl proton), 8.32 (1H, S., H-2), 8.75 (1H, S., H-8), 11.14 (1H, broad, NH, exchanged by D$_2$O).

EXAMPLE 16

2'-deoxy neplanocin A 1) 2'-(R)-bromo-2'-deoxy-3',5'-O-(1,1,3,3-tetraisopropyl disiloxane-1,3-di-yl) neplanocin A (500 mg), tin tri-n-butyl hydride (0.35 ml) and a catalytic amount of azobisisobutyronitrile were dissolved in benzene (5 ml), and refluxed under an argon stream for 3 hours. The reaction mixture was concentrated in vacuo. The residue was purified by silica gel column chromatography using chloroform-ethanol (40:1). Fractions showing Rf$_3$=0.24 were collected and concentrated in vacuo. The residue was recrystallized from ethanol to obtain 2'-deoxy-3',5'-O-(1,1,3,3-tetraisopropyl disiloxane-1,3-di-yl) neplanocin A (385 mg, yield: 90%).

m.p.: 149°–151° C.

NMR: δppm (CDCl$_3$) 1.1 (28H, isopropyl), 2.3–2.6 (2H, 16 tet, H-2'), 4.49 (2H, S., H-5'), 5.39 (1H, d.d, H-3'), 5.72 (2H, S., NH2, exchanged by D$_2$O), 5.81 (2H, H-1' and H-6'), 7.75 (1H, S., H-2), 8.36 (1H, S., H-8).

UV: $\lambda_{max}^{MeOH}$ = 262 nm

Mass: 489 (M+), 446, 354, 311, 212, 136, 135.

Elementary analysis [C$_{23}$H$_{39}$O$_3$N$_5$Si$_2$½H$_2$O]:

|  | C % | H % | N % |
| --- | --- | --- | --- |
| Found: | 55.75 | 7.87 | 14.09 |
| Calculated: | 55.38 | 8.08 | 14.04 |

(2) The compound (278 mg) obtained in the above (1) and tetrabutylammonium fluoride (200 mg) were dissolved in anhydrous tetrahydrofuran (3 ml) and the mixture was stirred at room temperature for 10 minutes. The reaction mixture was concentrated in vacuo. The residue was recrystallized from ethanol to obtain 2'-deoxy neplanocin A (115 mg, yield: 82%).

m.p.: 231°–234° C.

Elementary analysis [C$_{11}$H$_{13}$O$_2$N$_5$]:

|  | C % | H % | N % |
| --- | --- | --- | --- |
| Found: | 53.43 | 5.25 | 28.04 |
| Calculated: | 53.43 | 5.30 | 28.33 |

TLC: Rf$_2$=0.17

NMR: δppm (DMSO-d$_6$) 2.2–2.4 (2H, m., H-2'), 4.15 (2H, slightly broad, H-5'), 4.8–5.0 (2H, t., +d.d., OH-5' and H-3'), 5.06 (1H, d., OH-3'), 5.64 (1H, m., H-1'), 5.75 (1H, J≃O, H-6'), 7.17 (2H, slightly broad, NH$_2$), 7.97 (1H, S., H-2), 8.13 (1H, S., H-8).

UV: $\lambda_{max}^{H2O}$ = 262 nm

Mass: 247 (M+), 229, 200, 186, 136, 135.

CD: [θ] −6,900 (252 nm, H$_2$O)

EXAMPLE 17

2'-(R)-amino-2'-deoxy neplanocin A acetate

2'-(R)-azide-2'-deoxy neplanocin A (80 mg) was dissolved in aqueous pyridine (50%, 5 ml). Hydrogen sulfide was bubbled therethrough at room temperature. The starting material disappeared wherein 6 hours and the reaction mixture was neutralized with 2 N-acetic acid, then concentrated in vacuo. Vacuum concentration was repeated twice by adding ethanol. Water was added to the residue and the insoluble material was removed. The supernatant solution was dried in vacuo. The residue was recrystallized from ethanol to obtain 2'-(R)-amino-2'-deoxy neplanocin A acetate (56 mg, yield: 72%).

TLC: Rf$_1$=0.15, Rf$_2$=0

NMR: δppm (DMSO-d$_6$) 2.50 (3H, S., CH$_3$COO−), 3.29 (3H, broad, $N^+H_3$), 3.47 (1H, d.d., H-2'), 4.14 (2H, S., H-5'), 4.49 (1H, d., H-3'), 4.85 (1H, broad, OH-3' or OH-5'), 5.22 (1H, broad, OH-5' or OH-3'), 5.46 (1H, d., H-1'), 5.71 (1H, J≃O, H-6'), 7.17 (2H, slightly broad, NH$_2$), 7.84 (1H, S., H-2), 8.12 (1H, S., H-8).

UV: $\lambda_{max}^{H2O}$ = 262 nm

Mass: 262 (M+), 244, 216, 186, 136, 135.

CD: [θ] −10,000 (252 nm, H$_2$O)

EXAMPLE 18

$N^6$-benzoyl-2'-deoxy neplanocin A (1) 2'-iodo-3',5'-O-(1,1,3,3-tetraisopropyl disiloxane-1,3-di-yl)-$N^6$-benzoyl neplanocin A (230 mg), a catalytic amount of azobisisobutyronitrile, and tin tributyl hydride (0.089 ml), dissolved in anhydrous benzene, were refluxed for 1 hour. The reaction mixture was concentrated in vacuo and purified by silica gel column chromatography using chloroform-ethanol (40:1) to obtain $N^6$-benzoyl-2'-deoxy-3',5'-O-(1,1,3,3-tetraisopropyl disiloxane-1,3-di-yl) neplanocin A.

TLC: Rf$_1$=0.30, Rf$_4$=0.40

Mass: 593 (M+), 550, 354, 316, 311, 240, 105.

(2) The product obtained hereinabove and tetrabutylammonium fluoride (100 mg) were dissolved in tetrahydrofuran (1 ml), and stirred at room temperature for 10 minutes. The reaction mixture was concentrated, charged on a TLC plate and developed by chloroform-methanol (7:1). The band showing Rf$_2$=0.41 was collected, extracted with chloroform-methanol (5:1), concentrated in vacuo, then treated with diethyl ether to obtain a powder of $N^6$-benzoyl-2'-deoxy neplanocin A (52 mg).

NMR: δppm (DMSO-d$_6$) 2.4 (2H, m., H-2'), 4.18 (2H, slightly broad, H-5'), 4.9–5.0 (2H, t.t., d.d., H-3' and OH-5'), 5.14 (1H, d., OH-3'), 5.82 (2H, H-6' and H-1'), 7.5–7.7 (3H, m., phenyl proton), 8.0–8.1 (2H, m., phenyl proton), 8.33 (1H, S., H-2), 8.72 (1H, S., H-8), 11.12 (1H, broad, NH).

Mass: 351 (M+), 350, 240, 136, 135.

EXAMPLE 19

2'-(R)-acetylthio-2'-deoxy neplanocin A (1) 2'-0-trifluoromethanesulfonyl-3',5'-0-(1,1,3,3-tetraisopropyl disiloxane-1,3-di-yl) neplanocin A (1.9 g) and potassium thioacetate (0.62 g) were dissolved in hexamethylphosphoramide (20 ml) and the mixture was stirred at room temperature for 3 hours. The reaction mixture was poured into ice water. The precipitate was filtered, washed with water and again dissolved in chloroform. The solution was charged on a column of silica gel and eluted with benzene-ethyl acetate (1:2) to obtain a powder of 2'-(R)-acetylthio-2'-deoxy-3',5'-O-(1,1,3,3-tetraisopropyl disiloxane-1,3-di-yl) neplanocin A (1.55 g).

TLC: $Rf_6 = 0.19$

NMR: $\delta$ppm (CEDl$_3$) 1.1 (28H, isopropyl), 2.11 (3H, S., —S—COCH$_3$), 4.38 (1H, t., H-3'), 4.46 (2H, slightly broad, H-5'), 5.38 (1H, d.d., H-2'), 5.64 (2H, slightly broad, NH$_2$, exchanged by D$_2$O), 5.75 (1H, d.d., H-1'), 5.85 (1H, J$\approx$O, H-6'), 7.59 (1H, S., H-2), 8.28 (1H, S., H-8).

Mass: 563 (M$_+$), 520 (M$^+$ −43), 488, 353, 136, 135.

(2) Tetrabutylammonium fluoride (about 100 mg) was added to the above product (110 mg) dissolved in dry tetrahydrofuran (2 ml), and the mixture was stirred at room temperature for 5 minutes. The reaction mixture was concentrated in vacuo and the residue was dissolved in methanol which was immediately neutralized with aqueous acetic acid, then charged on a silica gel TLC plate. The band showing $Rf_2 = 0.23$ was collected after developing with chloroform-methanol (5:1). The extract was dried in vacuo to obtain powdery 2'-(R)-acetylthio-2'-deoxy neplanocin A (55 mg, yield: 88%).

TLC: $Rf_2 = 0.23$

UV: $\lambda_{max}^{H2O} = 262$ nm

CD: $[\theta]$ −42000 (262 nm, H$_2$O)

NMR (FX-200-FT, DMSO-d$_6$): $\delta$ppm (TMS) 2.10 (3H, S., acetylthio), 4.12 (1H, d.d., H-2'), 4.16 (2H, slightly broad, H-5'), 4.91 (2H, m., OH-3' or OH-5' and H-3', changed to 1H, d. upon addition of D$_2$O), 5.61 (2H, m., OH-3' or OH-5' and H-1', changed to 1H, d. by addition of D$_2$O), 5.80 (1H, J$\approx$O, H-6'), 7.17 (2H, slightly broad, NH$_2$-6, disappeared upon addition of D$_2$O), 7.86 (1H, S., H-2), 8.08 1H, S., H-8).

What is claimed is:

1. 2'-Deoxyneplanocin A of the formula:

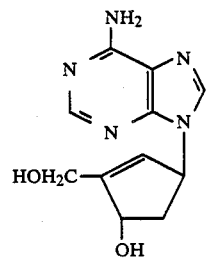

or a pharmaceutically acceptable salt thereof.

* * * * *